United States Patent [19]

Hardgrove

[11] Patent Number: Plant 7,417

[45] Date of Patent: Jan. 8, 1991

[54] MINIATURE ROSE PLANT DOHHAWK

[75] Inventor: Donald Hardgrove, El Cajon, Calif.

[73] Assignee: NOR'EAST Miniature Roses, Inc., Rowley, Mass.

[21] Appl. No.: 391,480

[22] Filed: Aug. 10, 1989

[51] Int. Cl.[5] ..... A01H 5/00

[52] U.S. Cl. ..... Plt./10

[58] Field of Search ..... Plt./10

*Primary Examiner*—James R. Feyrer

*Attorney, Agent, or Firm*—Christie, Parker & Hale

[57] ABSTRACT

A new variety of miniature rose having dark red flowers of good exhibition form.

1 Drawing Sheet

SUMMARY OF THE INVENTION

The present invention relates to a new and distinct variety of rose plant of the miniature rose class, which was originated by my crossing as seed parent the variety known as "Quinella" and as pollen parent the rose known as "Poker Chip". The varietal denomination of this new rose of "Dohhawk".

Among the novel characteristics possessed by this new variety which distinguishes it from its parents and all other varieties of which I am aware are its attractive dark red flowers of good exhibition form borne on a plant suitable for growing outdoor in gardens. Asexual reproduction by propagation by cuttings of the new variety as performed in San Bernardino Calif., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in color illustration of this character.

BRIEF DESCRIPTION OF THE DRAWINGS

The illustration depicts the attractive dark red flowers produced by the new variety of miniature rose.

DESCRIPTION OF PREFERRED EMBODIMENT

The following is a detailed description of my new variety, with color terminology in accordance with The Royal Horticultural Society Colour Chart (R.H.S.C.C.) and horticultural terminology in accordance with standard terminology used in UPOV-approved horticultural guidelines. The terminology used in color description herein refers to plate numbers in the aforementioned color chart.

Parentage: Seedling.

*Seed parent.*—"Quinella".

*Pollen parent.*—"Poker Chip".

Class: Miniature.

The following further horticultural observations were made of specimens grown outdoor in San Bernardino County, Calif., in the month of March.

FLOWER

Blooming habit: Recurrent.

A. Bud:

(1) *Size.*—Medium for miniature rose.

(2) *Form.*—Pointed, high centered.

(3) *Color.*—As sepals just separate, near 53A; after sepals divide, near 46A.

(4) *Sepals.*—Longer than bud, slightly foliated.

(5) *Penduncle.*—Length — about 1¼ inches. Aspect — straight. strength — erect. Color — near 184B.

B. Bloom: flower:

(1) *Size.*—Average size when fully expanded — about 1¼ inches.

(2) *Borne.*—Singly, one to a stem, and in small clusters.

(3) *Form.*—High centered at first, becoming flat; outer petals roll under.

(4) *Petalage.*—Number of petals under normal conditions — about 25 to 30, fully double.

(5) *Color.*—After sepals fall and petals unfurl, predominant flower color viewing petals' top surface is dark red near 46A to B. Color through this range is substantially stable. But, as blossoms mature, flower coloring tends to lighten and dark red coloring becomes less intense. Petals are near 12A toward point of petal attachment.

C. Petals:

(1) *Texture.*—Thick.

(2) *Appearance.*—Inside velvety and outside satiny.

(3) *Form.*—Obovate, fan shaped.

(4) *Arrangement.*—Regularly arranged, imbricated.

(5) *Petaloids in center.*—Medium.

(6) *Persistence.*—Drop off cleanly.

(7) *Fragrance.*—Slight to none.

(8) *Lasting quality.*—Long lasting quality on plant and as cut flower.

REPRODUCTIVE ORGANS

A. Stamens, filaments and anthers:

*Arrangement and Color.*—Regularly arranged around styles; color—filaments near 22A.

B. Pollen:

*Color.*—Near 22A.

C. Styles: Even, medium length, bunched.

D. Stigmas: Full.

E. Hips: None observed.

PLANT

A. Form: Upright.

B. Growth: Very vigorous, uniform branching.

Height attained.—about 18 to 24 inches.

C. Foliage: Compound 3, 5 and 7 leaflets.

(1) *Size.*—Medium for a miniature.
(2) Quantity.—Abundant.
(3) *Color.*—Foliage at time of first flowering — medium to dark green. New foliage: upper side near 59A; under side near 144A, flushed near 59C. Old foliage: upper side, near 147A; under side, near 147C.
(4) *Shape.*—Oval, pointed.
(5) *Texture.*—Upper side is semi glossy; under side is matte.
(6) *Edge.*—Serrate.
(7) *Serration.*—Ordinary, acuminate apices.
(8) Leaf stem.—Color — medium to dark green, near 141B to C.
(9) *Stipules.*—Smooth.

D. Wood:

(1) *New wood.*—Color — near 184A, smooth bark.
(2) *Old wood.*—Color — near 146B, smooth bark.

E. Prickles (thorns):
(1) *Prickles.*—Quantity (main stalk)— ordinary; on laterals from stalk — few; form — straight, small; color — near 184C; position — irregular.

F. Winter hardiness: Needs protection outdoors in severe climates.

I claim:

1. A new and distinct variety of rose plant of the miniature rose class, substantially as shown and described, characterized particularly by attractive dark red flowers of good form which are long lasting on the plant and after cutting.

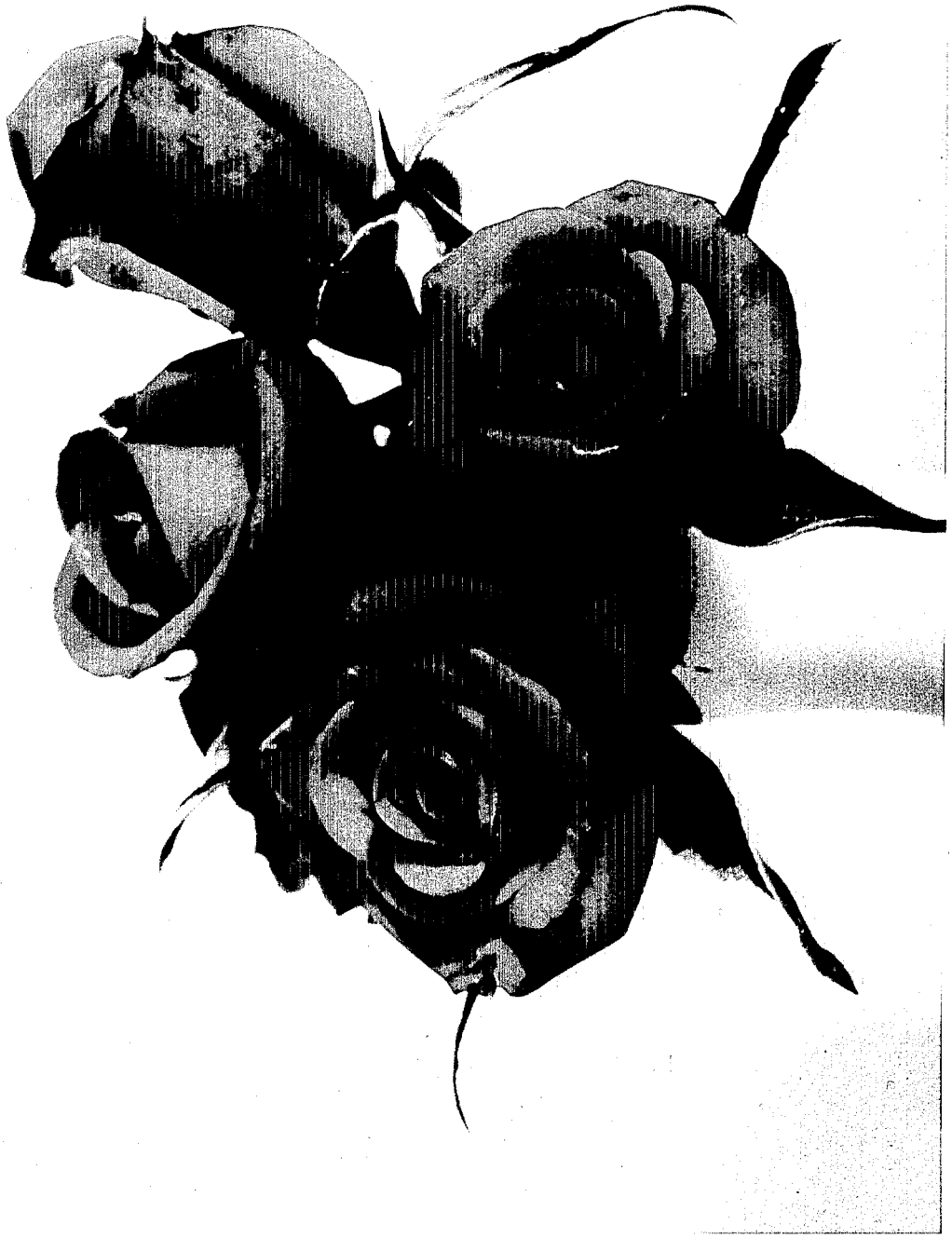

* * * * *